US00PP18487P2

(12) United States Plant Patent
Kanaya et al.

(10) Patent No.: US PP18,487 P2
(45) Date of Patent: Feb. 12, 2008

(54) ***PETUNIA* PLANT NAMED 'SUNSURFMICTROUT'**

(50) Latin Name: *Petunia×hybrida*
Varietal Denomination: Sunsurfmictrout

(75) Inventors: Takeshi Kanaya, Shiga (JP); Kazunari Iwaki, Shiga (JP); Yasuko Isobe, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/583,582

(22) Filed: Oct. 19, 2006

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Petunia* plant named 'Sunsurfmictrout', characterized by its outwardly spreading and mounding plant habit; vigorous growth habit; freely branching and flowering plant habit; long flowering period; and medium-sized light red-colored flowers.

1 Drawing Sheet

Botanical designation: *Petunia×hybrida.*
Cultivar denomination: 'Sunsurfmictrout'.

BACKGROUND OF THE INVENTION

The present invention relates to a new and distinct cultivar of *Petunia,* botanically known as *Petunia×hybrida* and hereinafter referred to by the name 'Sunsurfmictrout'.

The new *Petunia* is a product of a planned breeding program conducted by the Inventors in Shiga, Japan. The objective of the breeding program is to create new *Petunia* cultivars with attractive foliage and flower coloration.

The new *Petunia* originated from a cross-pollination made by the Inventors in September, 2003 in Shiga, Japan of a proprietary selection of *Petunia×hybrida* identified as code number PS105-3, not patented, as the female, or seed, parent with a proprietary selection of *Petunia×hybrida* identified as code number PS143-1, not patented, as the male, or pollen, parent. The new *Petunia* was discovered and selected by the Inventors as a single flowering plant within the progeny of the stated cross-pollination in a controlled environment in Shiga, Japan.

Asexual reproduction of the new *Petunia* by terminal cuttings in a controlled environment in Shiga, Japan since September, 2005, has shown that the unique features of this new *Petunia* are stable and reproduced true to type in successive generations.

SUMMARY OF THE INVENTION

The cultivar Sunsurfmictrout has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunsurfmictrout'. These characteristics in combination distinguish 'Sunsurfmictrout' as a new and distinct cultivar of *Petunia:*

1. Outwardly spreading and mounding plant habit.
2. Vigorous growth habit.

3. Freely branching and flowering plant habit.
4. Long flowering period.
5. Medium-sized light red-colored flowers.

Plants of the new *Petunia* can be compared to plants of the female parent selection. Plants of the new *Petunia* differ from plants of the female parent selection in the following characteristics:

1. Plants of the new *Petunia* are larger than plants of the female parent selection.
2. Plants of the new *Petunia* have larger flowers than plants of the female parent selection.

Plants of the new *Petunia* can be compared to plants of the male parent selection. Plants of the new *Petunia* differ from plants of the male parent selection in the following characteristics:

1. Plants of the new *Petunia* are more compact and mounding than plants of the male parent selection.
2. Plants of the new *Petunia* and the male parent selection differ in flower color as plants of the male parent selection have light pink-colored flowers.

Plants of the new *Petunia* can also be compared to plants of the cultivar Sunpatire, disclosed in U.S. Plant Pat. No. 15,756. In side-by-side comparisons conducted in Shiga, Japan, plants of the new *Petunia* and the cultivar Sunpatire differed in the following characteristics:

1. Plants of the new *Petunia* were more compact than and not as spreading as plants of the cultivar Sunpatire.
2. Plants of the new *Petunia* had smaller flowers than plants of the cultivar Sunpatire.
3. Plants of the new *Petunia* and the cultivar Sunpatire differed in flower color as plants of the cultivar Sunpatire had red purple-colored flowers.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia*.

The photograph at the top of the sheet comprises a top perspective view of a typical flowering plant of 'Sunsurfmictrout' grown in a container.

The photograph at the bottom of the sheet comprises a close-up of typical flowers of 'Sunsurfmictrout'.

DETAILED BOTANICAL DESCRIPTION

The photographs and following observations, measurements and values describe plants grown in Shiga, Japan, under commercial practice during the spring in an outdoor nursery day temperatures averaging 21° C. and night temperatures averaging 14° C. Plants grown for about four months with one plant per 13.5-cm container and pinched one time. In the following description, color references are made to The Royal Horticultural Society Colour Chart, 2001 Edition, except where general terms of ordinary dictionary significance are used.

Botanical classification: *Petunia×hybrida* cultivar Sunsurfmictrout.

Parentage:

*Female, or seed, parent.*—Proprietary selection of *Petunia×hybrida* identified as code number PS105-3, not patented.

*Male, or pollen, parent.*—Proprietary selection of *Petunia×hybrida* identified as code number PS143-1, not patented, Propagation:

*Type.*—By terminal cuttings.

*Time to initiate roots.*—About one week at temperatures of 20° C. to 25° C.

*Time to produce a rooted young plant.*—About three weeks at temperatures of 20° C. to 25° C.

*Root description.*—Fine, fibrous; light brown in color.

*Rooting habit.*—Freely branching.

Plant description:

*Plant and growth habit.*—Outwardly spreading and mounding plant habit. Freely branching with lateral branches potentially developing at every node; pinching enhances lateral branch development. Vigorous growth habit.

*Plant height.*—About 11.2 cm.

*Plant diameter.*—About 41.6 cm.

Lateral branch description:

*Length.*—About 19.8 cm.

*Diameter.*—About 2.5 cm.

*Internode length.*—About 1 cm.

*Strength.*—Strong.

*Aspect.*—Initially upright to outward.

*Texture.*—Pubescent.

*Color.*—144A.

Foliage description:

*Arrangement.*—Before flowering, alternate, simple; after flowering, opposite, simple.

*Length.*—About 5.4 cm.

*Width.*—About 2.4 cm.

*Shape.*—Ovate.

*Apex.*—Acute.

*Base.*—Obtuse.

*Margin.*—Entire.

*Texture, upper and lower surfaces.*—Pubescent; viscid.

*Venation pattern.*—Pinnate; reticulate.

*Color.*—Developing and fully expanded foliage, upper surface: 137B; venation, 144B. Developing and fully expanded foliage; lower surface: 137C; venation, 144B.

*Petiole.*—Length: About 8 mm. Diameter: About 1.3 mm. Texture, upper and lower surfaces: Pubescent. Color, upper and lower surfaces: 144B.

Flower description:

*Flower arrangement and habit.*—Single salverform flowers arising from leaf axils. Freely flowering habit with usually about 31 flowers developing per plant. Flowers not persistent. Flowers face upright or outwardly. Flowers not fragrant.

*Natural flowering season.*—Plants of the new *Petunia* initiate and develop flowers about two to three weeks after planting. Long flowering period; flowering commences naturally during the spring and plants flower continuously throughout the summer until the fall in Japan.

*Flower longevity.*—Individual flowers last about five days on the plant.

*Flower diameter.*—About 4.7 cm.

*Flower length (depth).*—About 3 cm.

*Throat diameter.*—About 7.7 mm.

*Tube diameter.*—About 2.2 mm.

*Flower bud.*—Shape: Cylindrical. Length: About 3.4 cm. Diameter: About 5.5 mm. Color: N77D.

*Corolla.*—Arrangement: Five petals fused at the base and opening into a flared trumpet. Petal length from throat: About 1.7 cm. Petal width: About 2.2 cm. Petal shape: Broadly obovate. Petal apex: Mucronate. Petal margin: Entire; slightly undulate. Petal texture, upper and lower surfaces: Smooth, glabrous; satiny. Tube texture: Pubescent. Color: Petal, when opening, upper surface: 45B; venation, N199B. Petal, when opening, lower surface: 181D. Petal, fully opened, upper surface: 51A; venation, N199C. Petal, fully opened, lower surface: 54C. Throat: 150D; venation, 183A. Tube: 184B.

*Calyx.*—Arrangement: One star-shaped calyx tube with five sepals fused at the base per flower. Sepal length: About 1.2 cm. Sepal width: About 2.6 mm. Sepal shape: Narrowly elliptic. Sepal apex: Rounded. Sepal margin: Entire. Sepal texture, upper and lower surfaces: Pubescent. Color, upper surface: 137B. Color, lower surface: 137C.

*Peduncles.*—Length: About 2.5 cm. Diameter: About 1 mm. Angle: About 45° from vertical. Strength: Strong. Texture: Pubescent; viscid. Color: 144A.

*Reproductive organs.*—Stamens: Quantity/arrangement: Five per flower. Anther shape: Ellipsoidal. Anther size: About 2 mm by 2 mm. Anther color: 155B. Pollen amount: Moderate. Pollen color: 155B. Pistils: Quantity: One per flower. Pistil length: About 1.7 cm. Style color: 144B. Stigma shape: Transversely ellipsoidal. Stigma color: 144B. Ovary color: 144A. Seed/fruit: Seed and fruit development have not been observed on plants of the new *Petunia*.

Temperature tolerance: Plants of the new *Petunia* have been observed to tolerate temperatures from about 5° C. to about 35° C.

Pathogen/pest resistance: Plants of the new *Petunia* have not been observed to be resistant to pests and pathogens common to *Petunia*.

It is claimed:

1. A new and distinct *Petunia* plant named 'Sunsurfmictrout' as illustrated and described.

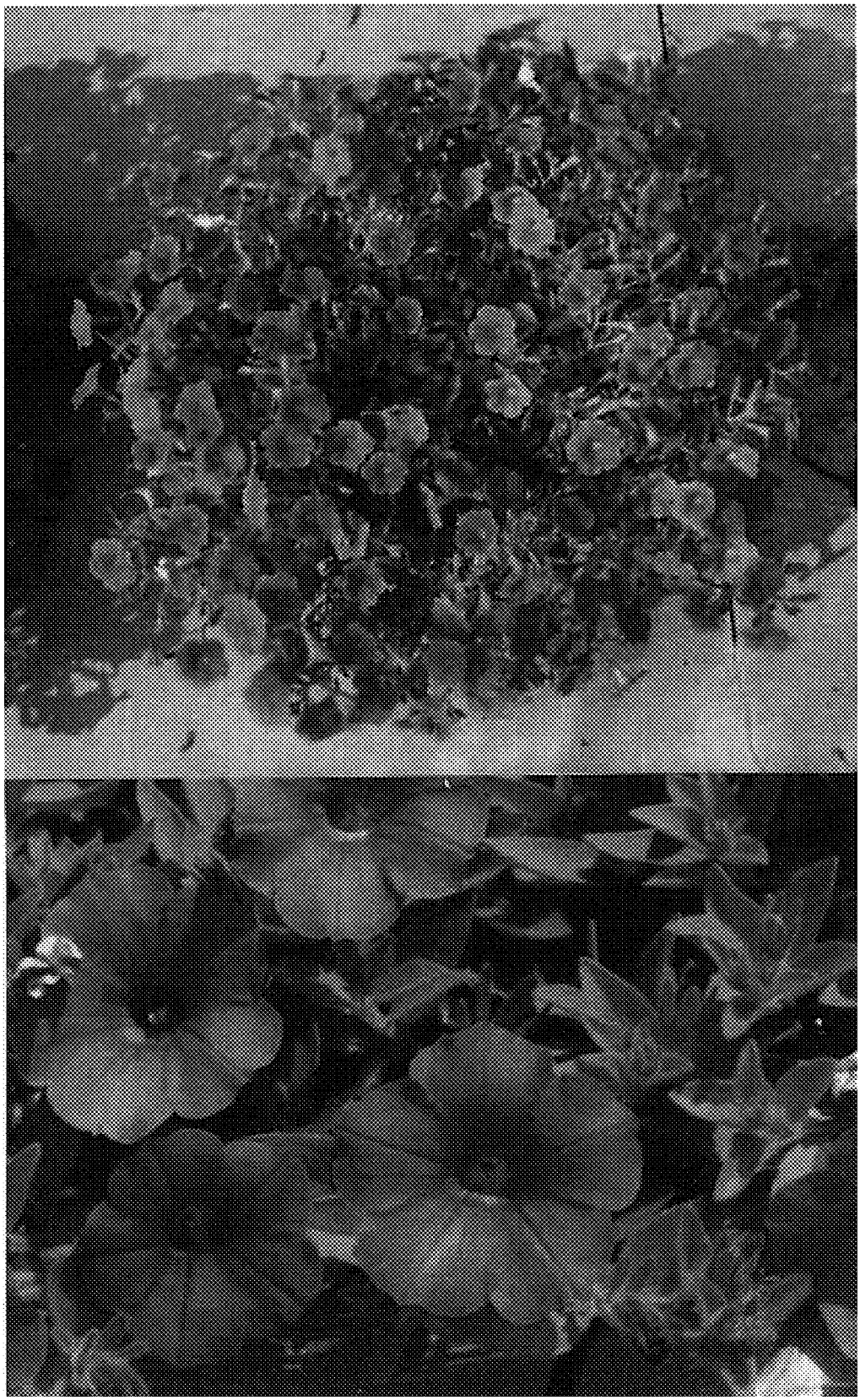

* * * * *